United States Patent [19]
Clark et al.

[11] Patent Number: 5,354,261
[45] Date of Patent: Oct. 11, 1994

[54] FLUID-RETENTIVE BANDAGE

[76] Inventors: Francis S. Clark, 5838 Club View Dr., Ogden, Utah 84403; Warren D. Hansen, 8378 Azul Way, Sandy, Utah 84093

[21] Appl. No.: 902,687

[22] Filed: Jun. 22, 1992

[51] Int. Cl.$^5$ .................... A61F 13/00; A61F 15/00
[52] U.S. Cl. ........................................ 602/58; 602/42; 128/888; 128/854
[58] Field of Search ............. 128/887, 888, 853, 854, 128/855; 602/42, 43, 47, 58, 59, 53; 604/304, 307, 336; 206/439

[56] References Cited

U.S. PATENT DOCUMENTS

| | | | |
|---|---|---|---|
| 1,920,808 | 8/1933 | Sander | 604/307 |
| 3,556,096 | 1/1971 | Fuller et al. | 602/58 |
| 3,921,629 | 11/1975 | Ekbladh | 128/888 |
| 4,221,215 | 9/1980 | Mandelbaum | 604/327 |
| 4,263,906 | 4/1981 | Finley | 602/79 |
| 4,399,816 | 8/1983 | Spangler | 128/888 |
| 4,753,230 | 6/1988 | Carus et al. | 602/47 |
| 4,890,608 | 1/1990 | Steer | 604/332 |
| 5,086,763 | 2/1992 | Hathman | 602/42 |
| 5,086,764 | 2/1992 | Gilman | 602/42 |
| 5,167,613 | 12/1992 | Karami et al. | 602/42 |
| 5,197,493 | 3/1993 | Grier-Idris | 602/58 |

FOREIGN PATENT DOCUMENTS 3907522 4/1990 Fed. Rep. of Germany ........ 602/53

Primary Examiner—Randall L. Green
Assistant Examiner—Paul Prebilic
Attorney, Agent, or Firm—Thompson E. Fehr; Daniel P. McCarthy; David B. Denoyer

[57] ABSTRACT

A bandage which retains bodily fluids at least until such fluids reach the top of the dressing that may be placed in the bandage and which permits removal or replacement of the dressing without detaching the bandage from the patient. The bandage has a holder with a base portion which is adhesively attached to the skin of the patient and which contains an aperture to accommodate a wound. Connected to the base portion is at least one flap which folds over the dressing that may be inserted into the holder and which has a releasable fastener to close the holder, to maintain the dressing in a desired position, and to enable the bandage to be opened for inspection of the wound or replacement of the dressing. Fluid retention is accomplished by having the distal (with respect to the patient) edge of no flap closer to the patient's body than is the distal side of the dressing. And when the holder is constructed of transparent material, medical care givers can readily observe as bodily fluids approach the distal side of the dressing. An optional embodiment includes a flat pad having an aperture similar to that of the base portion. The holder is bonded to the flat pad, with the apertures of each aligned with one another; the flat pad and, consequently, the holder, is subsequently adhesively attached to the patient.

8 Claims, 8 Drawing Sheets

FLUID-RETENTIVE BANDAGE

BACKGROUND OF THE INVENTION

1. Field of Invention

This invention relates generally to bandages and, in particular, to bandages having a wound dressing portion which may be readily removed or changed.

2. Description of the Related Art

In U.S. Pat. No. 4,221,215 Isidore Mandelbaum claims a folding dressing. One half of the dressing is attached to the skin of the patient and contains an opening to accommodate the semi-permanent presence of medical devices such as drainage tubes. Immediately upon removal of the medical device, the second half of the dressing is folded onto and attached to the first half to protect the wound and prevent it from becoming infected. Although some claims merely refer to an attaching means for connecting the two halves, only an adhesive is disclosed. There is, furthermore, no discussion of reopening the dressing once it has been folded and closed. And the dressing cannot be removed and replaced while leaving a container (bandage) for the dressing attached to the patient. Additionally, since the dressing is not covered with a material that is impervious to fluids, it would not necessarily retain bodily fluids.

Edward F. Klein, in U.S. Pat. No. 2,273,873, claimed a transparent, non-porous tape which is cut into strips and placed on the patient's skin around the wound. Then a transparent cover can be placed over the wound and attached to the strips, which have adhesive on both sides; a dressing can be placed over the wound and attached to the strips; or a dressing can be placed over the wound with the transparent cover going over the dressing and being attached to the strips. This device would only contain bodily fluids when the transparent cover is employed, access to the wound could only be obtained by cutting through the transparent cover or the dressing or both (necessitating subsequently taping over the cut) or by removing and then replacing the entire device, and the dressing could not be changed without removing and replacing the entire device.

The device claimed by Peter L. Steer in U.S. Pat. No. 4,890,608 consists of an adhesive pad for attachment to the skin surrounding a patient's wound together with a plurality of adhesive annuli for mounting to the pad a wound cover. The mounting of a dressing is also disclosed. An alternative embodiment consists of having a plurality of wound covers each containing adhesive. If a dressing is mounted on the pad, access to the wound would be achieved by removing the dressing and one of the adhesive annuli, since several annuli are stacked vertically and connected in such a manner that they can be peeled apart; this would create a burden of creating waste consisting of the dressing and an adhesive annulus each time the wound is inspected, the dressing would not be reusable, and the dressing would allow bodily fluids to leak. When only a wound cover is used, access would still involve the problem of creating waste—either an adhesive annulus or a wound cover, depending on the particular embodiment selected—(although the wound could be viewed through a transparent wound cover if access were not essential) and could also involve leakage of bodily fluids since the only discussion in the patent concerning retention of fluids applies solely to the adhesive contact of the pad with the skin.

A pad for holding liniment that can be buttoned to tabs which are attached with adhesive to the skin of the patient is claimed by Benjamin T. Jacobs in U.S. Pat. No. 437,994. No disclosure is made with respect to using the pad to cover a wound. If it were so used, however, the pad could be removed to inspect the wound and then be placed again upon the wound or could be replaced with a new pad; but it would allow bodily fluids to leak. And neither the tabs nor the pad would remove stress on the tissues surrounding a wound by urging the sides of an incision or laceration toward each other.

Michael S. Finley, in U.S. Pat. No. 4,263,906, claims a flexible base frame which is attached to the skin of a patient through the use of either sutures or adhesive and which utilizes either reusable clips or Velcro fasteners for attaching a flexible top frame to the base frame. The top frame is, furthermore, affixed (by any suitable means such as adhesive) to the marginal portions of a dressing. To inspect the wound, the dressing and the top frame could easily be removed and then returned. Although the patent asserts that changing of the bandage involves replacement of only the dressing, it would seem that, if the dressing had been attached to the top frame with adhesive, the top frame would also have to be replaced—creating additional waste. Most importantly, though, bodily fluids could leak through the connection between the top and base frames and, apparently, through the top frame because such frame seems to create only a border around (rather than a cover over) the dressing and because no assertion is made that the frames would be impermeable to fluids. And the seemingly significant distance between the base frame and many portions of the wound as well as the optional use of sutures or skin staples to affix the base frame to the skin would preclude the bandage from relieving stress on the tissues surrounding a wound by urging the sides of the incision or laceration toward each other.

Finally, U.S. Pat. No. 3,556,096 of John D. Fuller and Decla M. Fuller claims a bandage which is composed of two portions. The bottom portion is attached to the skin of the patient and contains a central aperture for a decubitus ulcer—the only affliction which the bandage is claimed to treat. The top portion may be permanently hinged to the bottom portion. The bottom portion may be placed over or under a dressing. (Because it is used for a decubitus ulcer, the bandage also contains a thick cushion.) The top portion is either folded over or placed onto the bottom portion and retained in place either by cords or nylon (Velcro) fasteners. If such a bandage were used to cover a wound, access to the wound could easily be accomplished with no waste of material, the dressing could be removed and replaced without consuming any other component, and the edges of a wound would be urged toward one another by the adhesively attached bottom portion of the bandage. Bodily fluids would, however, readily leak from the bandage.

SUMMARY OF THE INVENTION

The instant invention provides access to a wound with no waste of material. The dressing can be removed to facilitate such access and can then be returned to its original location within the bandage with no consumptive use of material. Alternatively, the dressing can be replaced with a new dressing without having as waste anything more than the old dressing.

The bandage will remove stress on the tissues surrounding a wound by urging the sides of the incision or laceration toward each other. And, of greatest importance in view of the fact that bodily fluids provide a medium for the transmission of the human immunodeficiency virus associated with acquired immune deficiency syndrome, the instant invention will, in the vast majority of situations where it is employed, retain bodily fluids which emanate from the wound.

None of the patents in the prior art possess all these advantages. In fact, only U.S. Pat. No. 2,273,873 of Edward F. Klein could clearly contain bodily fluids; and Klein's invention can do so only at the expense of having to cut and subsequently tape the transparent cover or replace the entire bandage if access to the wound is necessary or (when a dressing is utilized) even if it is desired simply to view the wound.

The primary element of the instant bandage is the holder. The holder is constructed of any material which is sufficiently flexible to bend to accommodate attachment to various portions of a patient's body as well as to adjust to the normal bodily movements of a recovering patient without detaching from the body, which is impermeable to bodily fluids, and which can be sterilized. Some examples of suitable materials are polyethylene film, polyurethane, plasticized polyvinylchloride, and polypropylene. In its preferred embodiment, the holder will be transparent and permeable for vapors. (As used herein the term "bodily fluids" refers, in its customary sense, solely to liquids.)

The holder consists of a single piece of the foregoing material. The base portion of the holder is to fit against the skin of the patient and, in the preferred embodiment, contains an aperture to accommodate the wound. In one alternative embodiment, the base portion contains only a small aperture to facilitate the cutting, by the medical care giver, of a larger aperture of he dimensions desired by such care giver.

Attachment of the base portion to the skin is accomplished by having coated the side of the base portion that will be beside the skin with a skin-compatible medical-grade adhesive. A protective cover (usually a form of paper) is removably attached to the adhesive-covered side of the base portion until shortly before the bandage is applied to the patient. In an alternative embodiment, a skin-compatible medical-grade bactericide that will not degrade the performance of the adhesive is mixed into the adhesive.

The shape of the base portion is similar to that of the region of the dressing which will touch the base portion of the holder after a dressing has been inserted into the holder. The remainder of the holder consists of at least one flap designed to fold over the dressing in such a manner as to minimize movement of the dressing within the holder. Closure of the flap or flaps is accomplished with a reusable fastener, preferably double-sided closing tape, i.e., tape having an adhesive on both of its flat surfaces that strongly adheres to the tape but only releasably adheres to the flap(s), although one could utilize a nylon tape fastener such as those sold under the registered trademark "Velcro", which have stiff cut loops that extend from a backing material to engage releasably the other side of the fastener—a napped fabric. The "Velcro" fasteners close firmly when both sides are pressed together with even a slight pressure; yet, the sides can be readily separated by pulling the sides apart with a tearing motion.

The flap or flaps are so designed that, when the flap or flaps are folded over the dressing, no distal portion of any flap is closer to the base portion of the holder than is the distal side of the dressing. Normally, the pain associated with an incision or laceration will cause a patient to lie with the wound as the most elevated portion of the patient's body. Consequently, even if the fastener which closes the flaps fails to form a seal that is impermeable to bodily fluids, there can be no leakage until bodily fluids reach the top of the dressing—a condition which would easily be anticipated and avoided when the transparent holder of the preferred embodiment is employed.

Since the fasteners and, thus, the flaps can be readily opened with no discomfort for the patient, the dressing can—even if the holder is not transparent—be inspected frequently and then removed and replaced with a new dressing to assure that no bodily fluids leak. As indicated above, the only item that would be consumptively used during this process is the dressing itself.

Besides preventing the leakage of fluids as discussed, the instant bandage also retains the wound within a sterile environment.

Access to the wound is achievable by simply opening the flaps and removing the dressing. When the desired activity has been completed, the dressing can be returned to the holder and the flaps, closed—all without (again, as mentioned above) producing any waste.

The holder and dressing can be constructed with any desired shape. For example, the base portion of the holder could be circular. In that event, the flap would be formed by merely continuing the circle sufficiently outward from the base portion that the additional material can be folded over the dressing so that material from any side overlaps that from the opposite side.

In the preferred embodiment, the base portion of the holder would, however, be rectangular. One end flap extends from each end of the base portion; and one side flap extends from each side of the base portion.

The end flaps are folded over the dressing first. Preferably, each side flap has a strip of the double-sided closing tape running longitudinally along its surface which is inside the holder when the flaps are closed. The double-sided closing tape on the first side flap to be closed would then adhere to the dressing to decrease the probability of undesired movement of the dressing within the holder and would also adhere to the two end flaps to assist in keeping the end flaps closed, and the double-sided closing tape on the second side flap to be closed would adhere to the other side flap to maintain the side flaps in a closed position. In an alternative embodiment, a strip of the double-sided closing tape runs longitudinally along the surface of only one side flap; again this is on the surface which is inside the holder when the side flaps are closed. The side flap having the double-sided closing tape would then have to be closed last. This would adhesively maintain the side flaps in a closed position. The end flaps would be held closed by friction and the side flaps.

To assure that no distal portion of any flap is, after being folded, closer to the base portion of the holder than is the distal side of the dressing, adjacent flaps do not meet at a ninety-degree angle on the edge of the base portion of the holder but are connected by extending the holder into the angle between adjacent flaps a distance that is at no point less than the thickness of the dressing.

When the flaps are closed, the extended portion of the holder between adjacent flaps will necessarily result in an internal fold where adjacent flaps meet. If it is desired that such internal fold not exist when the holder has been closed, the base portion of the holder can be composed of the same rectangular structure discussed above plus sections at each end and each side of the rectangular structure which extend distally (with respect to the patient) outward from the rectangular structure the same distance as does the dressing. The end flaps and side flaps are then attached to the base portion on its distal edges. Thus, as viewed from directly overhead, the holder would appear identical to the preferred embodiment except that the holder would not be extended into the angle between adjacent flaps because the function of retaining bodily fluids would be performed primarily by the distally outward sections.

The aperture in the base portion of the holder may, also, be of any desired shape, although a rectangle would be preferred to accommodate wounds from incisions.

Similarly, dimensions of the bandage can be as desired.

Another alternative embodiment has bonded to the proximal (with respect to a patient) side of the base portion of the holder a flat pad to fit against the skin of a patient, made from the same material as the holder, shaped similarly to the base portion of the holder, having an outer dimension slightly larger than such base portion, and possessing a pad aperture shaped and sized similarly to the aperture in the base portion of the holder and located so that the pad aperture is aligned with the aperture of the base portion of the holder. In this embodiment the flat pad and, thus, the holder is attached to the skin of the patient by coating the side of the flat pad that will be beside the skin with a skin-compatible medical-grade adhesive. The flat pad is bonded to the holder by the adhesive on the holder, which adhesive would then not have to be skin compatible, or by heat welding, in which case the holder would contain no adhesive or protective cover. A protective cover (usually a form of paper) is, however, removably attached to all adhesive-covered surfaces of the flat pad until shortly before the bandage is applied to the patient. Utilizing the flat pad relieves stress on the bandage-to-skin adhesive connection when the flaps of the holder are opened and closed. In an alternative embodiment, a skin-compatible medical-grade bactericide that will not degrade the performance of the adhesive is mixed into the adhesive. When the alternative embodiment of the holder having in the base portion only a small aperture to facilitate the cutting, by the medical care giver, of a larger aperture of the dimensions desired by such care giver is utilized, an alternative embodiment of the flat pad having a small pad aperture shaped and sized similarly to the small aperture in the base portion of the holder is employed.

For all embodiments, several types of dressings can be utilized. In the preferred embodiment a traditional highly absorbent material, with—on its proximal (with respect to the patient) surface—a layer which will contact the wound and which is composed of material that will transmit bodily fluids from a wound to the highly absorbent material but that will not adhere to the wound, is utilized as the dressing. In an alternative embodiment, a releasably adhesive strip, such as double-sided stabilizing tape, i.e., tape having an adhesive on both of its flat surfaces that adheres strongly to the tape and to the dressing but only releasably adheres to the flaps, is connected to the distal (with respect to the patient) side of the dressing, which is otherwise constructed as described above, and, when the flaps are closed, to such flaps; this will decrease the probability of undesired movement of the dressing within the holder. And in an additional alternative embodiment, the highly absorbent layer is thin and surrounds a firm, absorbent core that swells upon absorbing bodily fluids, thereby maintaining pressure on the wound. All materials in the dressing are amenable to being sterilized.

Furthermore, in lieu of a dressing, a fluid-filled sack capable of being heated or cooled and having a relatively high specific heat capacity could be contained within the holder.

DESCRIPTION OF THE PREFERRED EMBODIMENT

Figure 1:
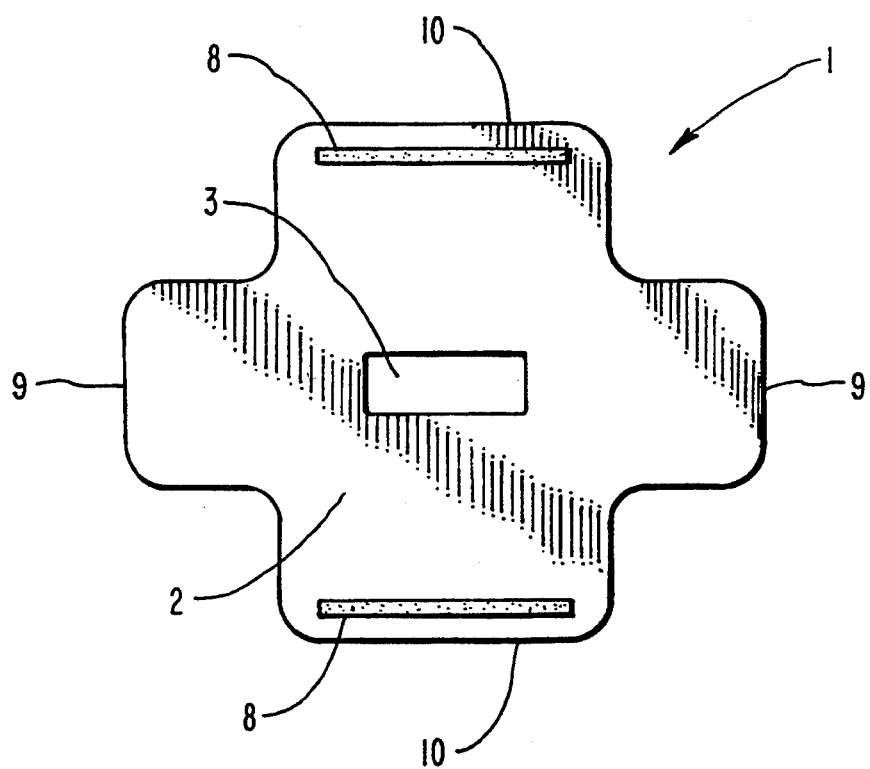
FIG. 1 shows the open holder as viewed from above.
Figure 2:
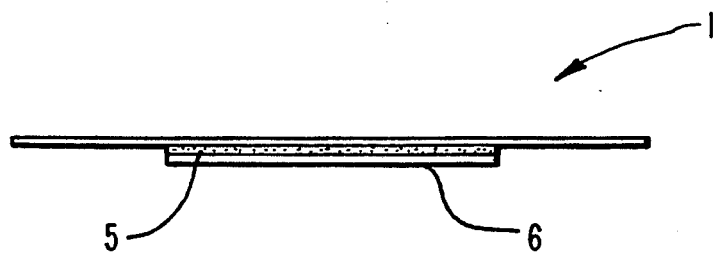
FIG. 2 is a lateral view of the open holder, with the adhesive and its protective cover enlarged for clarity.

The primary element of the fluid-retentive bandage is the holder (1), as shown in FIG. 1, FIG. 2, FIG. 5, FIG. 6, and FIG. 9.

The holder (1) is constructed of any material which is sufficiently flexible to bend to accommodate attachment to various portions of a patient's body as well as to adjust to the normal bodily movements of patient without detaching from the body, which is impermeable to bodily fluids, and which can be sterilized. Some examples of suitable materials are polyethylene film, polyurethane, plasticized polyvinylchloride, and polypropylene. In its preferred embodiment, the holder (1) will be transparent and permeable for vapors. (As used herein the term "bodily fluids" refers, in its customary sense, solely to liquids.)

The holder (1) consists of a single piece of the foregoing material. The base portion (2) of the holder (1) is to fit against the skin of the patient and, in the preferred embodiment, contains an aperture (3) to accommodate a wound. In one alternative embodiment, displayed in FIG. 5 and FIG. 6, the base portion (2) contains only a small aperture (4) to facilitate the cutting, by the medical care giver, of a larger aperture of such dimensions as are desired by such care giver.

Attachment of the base portion (2) to the skin is accomplished by having coated the side of the base portion (2) that will be toward the skin with a skin-compatible medical-grade adhesive (5), as illustrated in FIG. 2, FIG. 4, FIG. 6, and FIG. 8. A protective cover (6)—usually a form of paper—is removably attached to the adhesive-covered side of the base portion (2) until shortly before the bandage is applied to the patient. In an alternative embodiment, a skin-compatible medical-grade bactericide that will not degrade the performance of the adhesive (5) is mixed into the adhesive (5).

The shape of the base portion (2) is similar to that of the region of the dressing (7)—shown in FIG. 9, FIG. 15, FIG. 16, and FIG. 17—which will touch the base portion (2) of the holder (1) after a dressing (7) has been inserted into the holder (1). The remainder of the holder (1) consists of at least one flap designed to fold over the dressing (7) in such a manner as to minimize movement of the dressing (7) within the holder (1). Closure of the flap or flaps is accomplished with a reusable fastener, preferably double-sided closing tape (8), i.e., tape having adhesive on both of its flat surfaces that strongly adheres to the tape but only releasably adheres to the flap(s), although one could utilize a nylon tape fastener such as those sold under the registered trademark "Velcro", which have stiff cut loops that extend from a backing material to engage releasably the other side of the fastener—a naped fabric. The "Velcro" fasteners close firmly when both sides are pressed together with even a slight pressure; yet, the sides can be readily separated by pulling the sides apart with a tearing motion.

The flap or flaps are so designed that, when the flap or flaps are folded over the dressing (7), no distal portion of any flap is closer to the base portion (2) of the holder (1) than is the distal side of the dressing (7). Normally, the pain associated with an incision or laceration will cause a patient to lie with the wound as the most elevated portion of the patient's body. Consequently, even if the fastener which closes the flaps fails to form a seal that is impermeable to bodily fluids, there can be no leakage until bodily fluids reach the top of the dressing (7)—a condition which would easily be anticipated and avoided, especially when the transparent holder (1) of the preferred embodiment is employed.

Access to the wound is achievable by simply opening the flaps and removing the dressing (7). When the desired activity has been completed, the original or replacement dressing (7) can be returned to the holder (1); and the flaps can be closed.

The holder (1) and dressing (7) can be constructed with any desired shape. For example, the base portion (2) of the holder (1) could be circular. In that event, the flap would be formed by merely continuing the circle sufficiently outward from the base portion (2) that the additional material can be folded over the dressing (7) so that material from any side overlaps that from the opposite side.

In the preferred embodiment, the base portion (2) of the holder (1) is, however, rectangular. One end flap (9) extends—as demonstrated in FIG. 1, FIG. 5, and FIG. 9—from each end of the base portion (2); and one side flap (10) extends—as illustrated in FIG. 1, FIG. 5, and FIG. 9—from each side of the base portion (2).

The end flaps (9) are folded over the dressing (7) first. Preferably, each side flap (10) has a strip of the double-sided closing tape (8) running—as shown in FIG. 1, FIG. 5, and FIG. 9—longitudinally along its surface which is inside the holder (1) when the side flaps (10) are closed. The double-side closing tape (8) on the first side flap (10) to be closed would then adhere to the dressing (7) to decrease the probability of undesired movement of the dressing within the holder (1) and would also adhere to the two end flaps (9) to assist in keeping the end flaps (9) closed, and the double-sided closing tape (8 on the second side flap (10) to be closed would adhere to the other side flap (10) to maintain the side flaps (10) in a closed position. In an alternative embodiment, a strip of the double-sided closing tape (8) runs longitudinally along the surface of only one side flap (10); again this would be the surface which is inside the holder (1) when the side flaps (10) are closed. The side flap (10) having the double-sided closing tape (8) would then have to be closed last. This would adhesively maintain the side flaps (10) in a closed position. The end flaps (9) would be held closed by friction and the side flaps (10).

Figure 5:
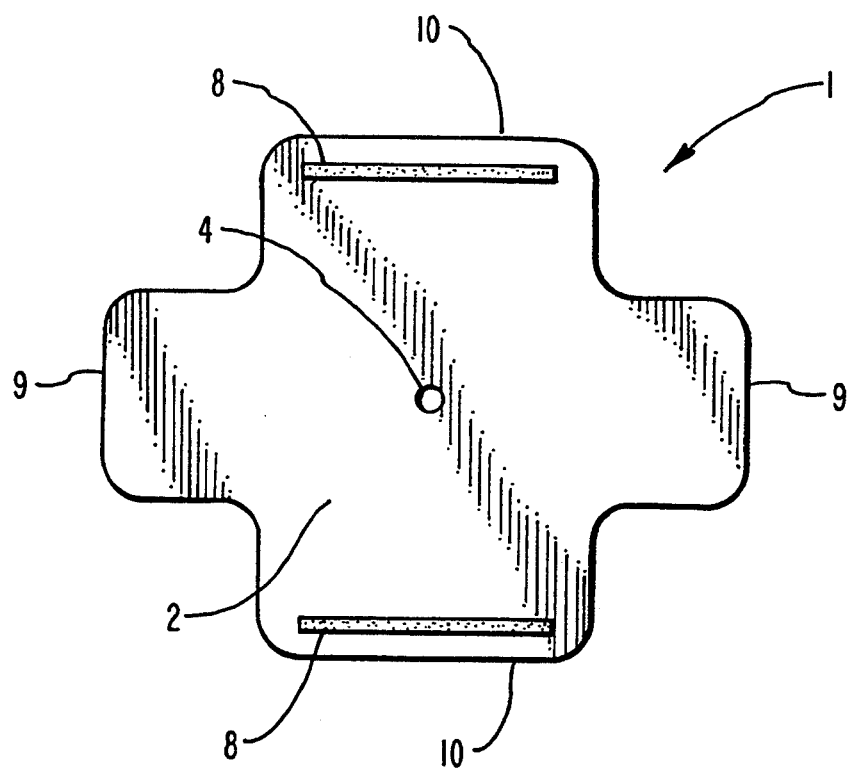
FIG. 5 demonstrates an alternative embodiment of the open holder as viewed from above.
Figure 6:
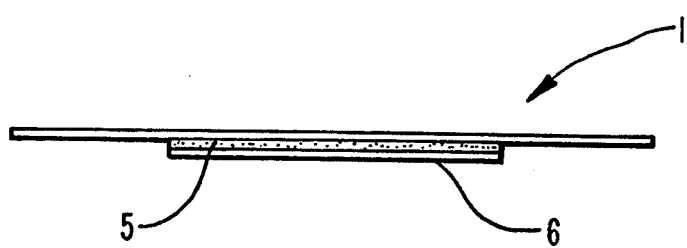
FIG. 6 gives a lateral view of an alterative embodiment of the open holder, with the adhesive and its protective cover enlarged for clarity.
Figure 9:
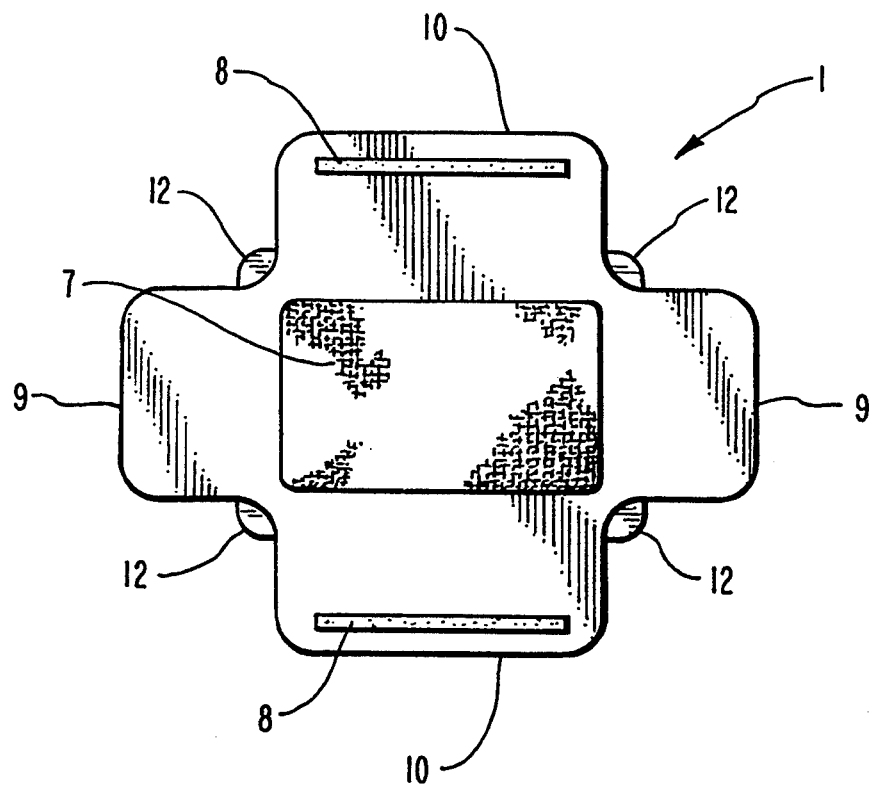
FIG. 9 provides an overhead view of the dressing on the open holder which has been attached to the flat pad.

To assure that no distal portion of any flap is, after being folded, closer to the base portion (2) of the holder (1) than is the distal side of the dressing (7), adjacent flaps do not—as shown in FIG. 1, FIG. 5, and FIG. 9—meet at a ninety-degree angle on the edge of the base portion (2) of the holder (1) but are connected by extending the holder (1) into the angle between adjacent flaps a distance that is at no point less than the thickness of the dressing (7).

Figure 7:
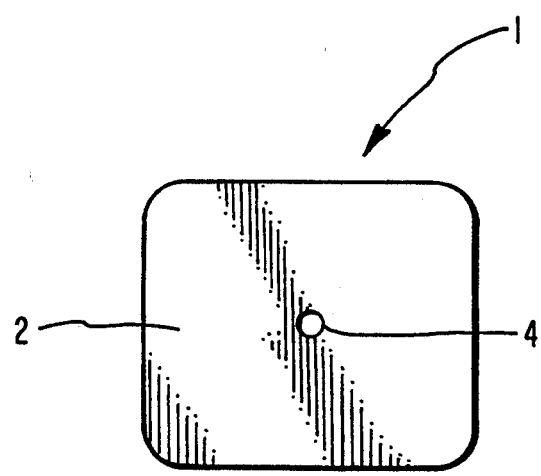
FIG. 7 depicts an alternative embodiment of the closed holder as viewed from below.
Figure 8:
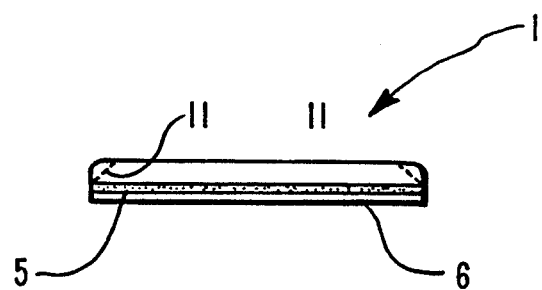
FIG. 8 displays a lateral view of an alternative embodiment of the closed holder, with the adhesive and its protective cover enlarged for clarity.
Figure 10:
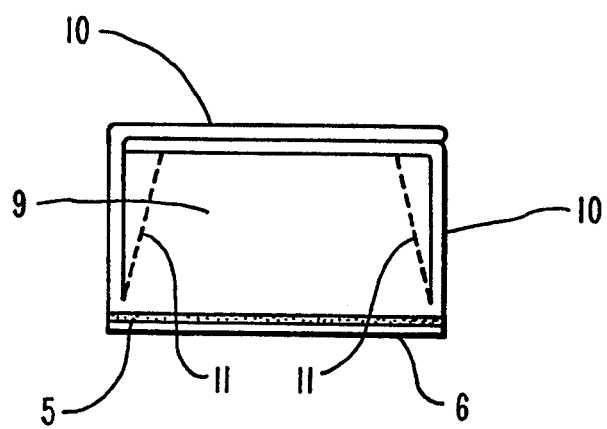
FIG. 10 views the closed holder from its end.

The holder (1) is shown with the flaps closed, as viewed from below in FIG. 3 and FIG. 7; as viewed from the side in FIG. 4 and FIG. 8; and as viewed from the end in FIG. 10. It is not essential that the side flaps (10) extend to the projected edge of the base portion (2) of the holder (1). The broken lines in FIG. 4, FIG. 8, and FIG. 10 indicates edges of the internal folds (11) that must be made upon folding the flaps to accommodate the extension of the holder (1) that exists between adjacent flaps.

Figure 11:
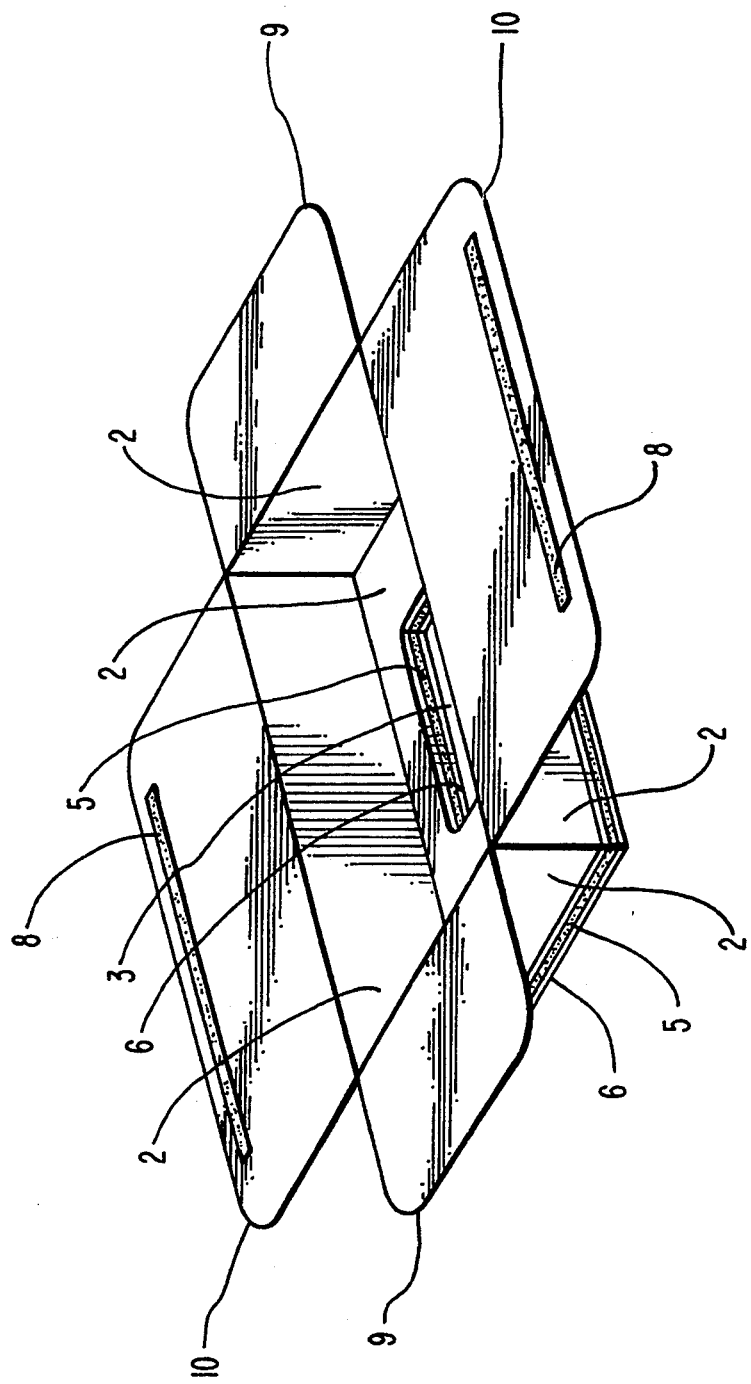
FIG. 11 is an isometric view of an open additional alternative embodiment of the holder, with the adhesive and its protective cover enlarged for clarity.

If it is desired that such internal folds (11) not exist when the holder (1) has been closed, the base portion (2) of the holder (1) can be constructed in the alternative embodiment illustrated in FIG. 11. In this embodiment, the base portion (2) is composed of the see rectangular structure discussed above plus sections at each end and each side of the rectangular structure which extend distally (with respect to the patient) outward from the rectangular structure the same distance as does the dressing (7). The end flaps (9) and side flaps (10) are attached to the base portion (2) on its distal edges. Thus, as viewed from directly overhead, the holder (1) would appear identical to the preferred embodiment except that the holder (1) would not be extended into the angle between adjacent flaps because the function of retaining bodily fluids would be performed primarily by the distally outward sections.

Figure 3:
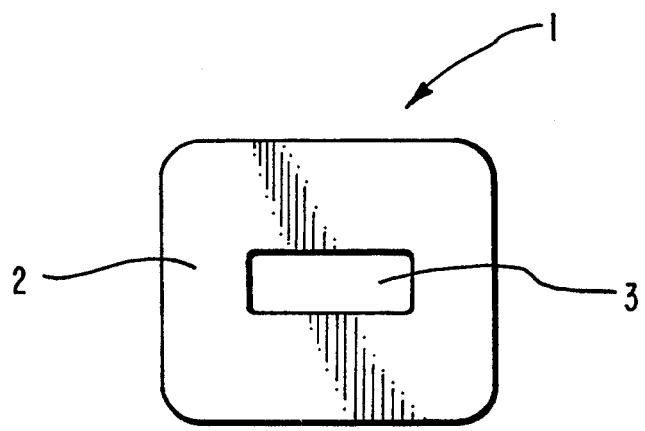
FIG. 3 portrays the closed holder as viewed from below.
Figure 4:
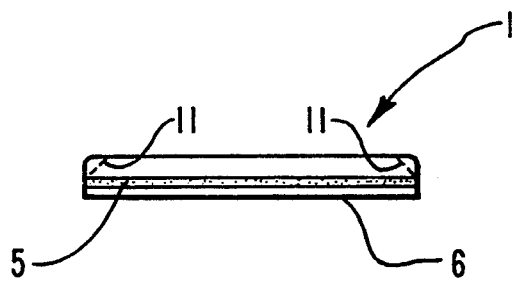
FIG. 4 presents a lateral view of the closed holder, with the adhesive and its protective cover enlarged for clarity.

The aperture (3) in the base portion (2) of the holder (1) may, also, be of any desired shape, although a rectangle—as shown in FIG. 1, FIG. 3, and FIG. 11—would be preferred to accommodate wounds from incisions.

Similarly, dimensions of the bandage can be as desired.

Figure 12:
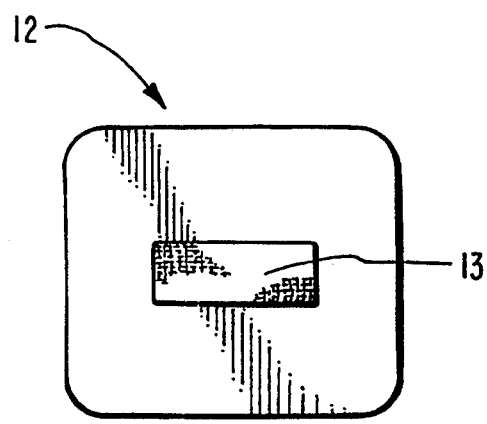
FIG. 12 displays the flat pad as viewed from above.
Figure 13:
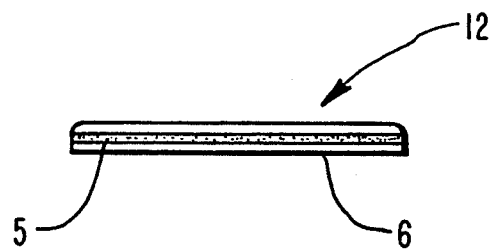
FIG. 13 provides a lateral view of the flat pad, with the adhesive and its protective cover enlarged for clarity.
Figure 14:
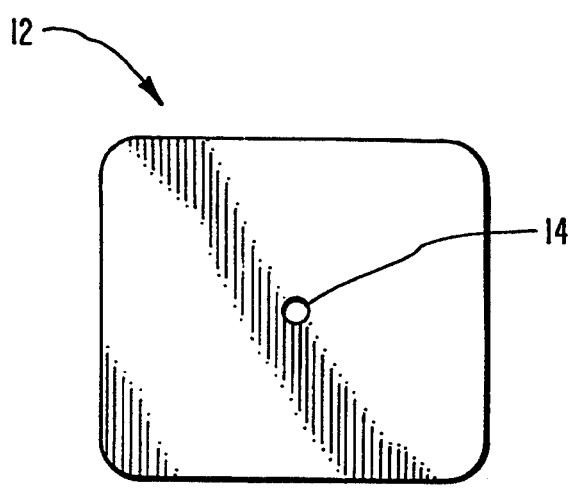
FIG. 14 shows an alternative embodiment of the flat pad as viewed from above.
Figure 15:
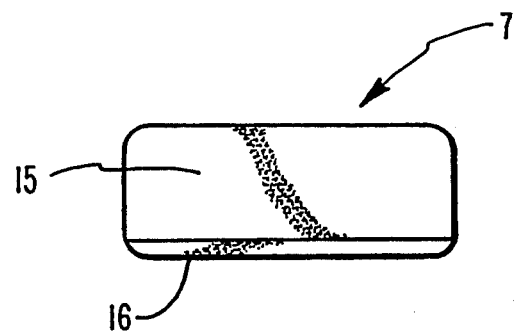
FIG. 15 displays a lateral view of the dressing.
Figure 16:
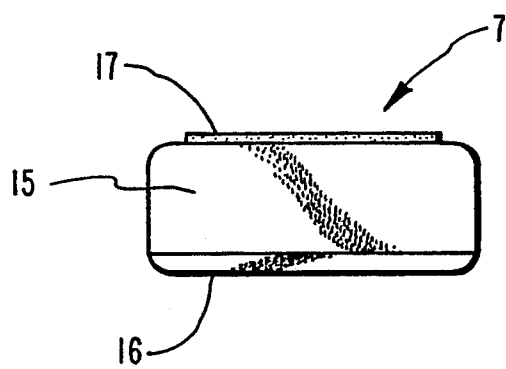
FIG. 16 demonstrates the dressing with double-side tape attached to it.
Figure 17:
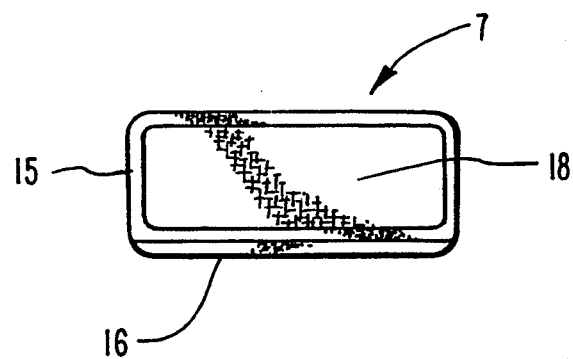
FIG. 17 portrays an alternative embodiment of the dressing.
Figure 18:
FIG. 18 is a lateral view of the holder with no adhesive or protective cover.

Another alternative embodiment has bonded to the proximal (with respect to a patient) side of the base portion (2) of the holder (1), a flat pad (12)—displayed in FIG. 9, FIG. 12, and FIG. 13—to fit against the skin of a patient, made from the same material as the holder (1), shaped similarly to the base portion (2) of the holder (1), having an outer dimension slightly larger than such base portion (2), and possessing a pad aperture (13) shaped and sized similarly to the aperture (3) in the base portion (2) of the holder (1) and located so that the pad aperture (13) is aligned with the aperture (3) in the base portion (2) of the holder (1). In this embodiment the flat pad (12) and, thus, the holder (1) is attached to the skin of the patient by coating the side of the flat pad (12) that will be beside the skin with a skin-compatible medical-grade adhesive (5). The flat pad (12) is bonded to the holder (1) by the adhesive (5) on the holder (1), which adhesive would then not have to be skin compatible, or by heat welding, in which case the holder (1) would—as shown in FIG. 18—contain no adhesive (5) or protective cover (6). A protective cover (6)—usually a form of paper—is, however, removably attached to all adhesive-covered surfaces of the flat pad (12) until shortly before the bandage is applied to the patient. In an alternative embodiment, a skin-compatible medical-grade bactericide that will not degrade the performance of the adhesive (5) is mixed into the adhesive (5). When the alternative embodiment of the holder (1) having in the base portion (2) only a small aperture (4) to facilitate the cutting, by the medical care giver, of a larger aperture of the dimensions desired by such care giver is utilized, an alternative embodiment of the flat pad (12)—displayed in FIG. 14—having a small pad aperture (14) shaped and sized similarly to the small aperture (4) in the base portion (2) of the holder (1) is employed.

For all embodiments, the dressing (7) can be selected from several different types. In the preferred embodiment—illustrated in FIG. 15—a traditional highly absorbent material (15), with—on its proximal (with respect to the patient) surface—a layer (16) which will contact the wound and which is composed of material that will transmit bodily fluids from a wound to the highly absorbent material (15) but that will not adhere to the wound, is utilized as the dressing (7). In an alternative embodiment—depicted in FIG. 16—a releasably adhesive strip, preferably double-sided stabilizing tape (17), i.e., tape having an adhesive, which is not necessarily the same as the skin-compatible medical-grade adhesive (5), on both of its flat surfaces that adheres strongly to the tape (17) and to the dressing (7) but only releasably adheres to the flaps, is connected to the distal (with respect to the patient) side of the dressing (7), which is otherwise constructed as described above, and, when the flaps are closed, to such flaps. And in an additional alternative embodiment—exhibited in FIG. 17, the highly absorbent material (15) is thin and surrounds a firm, absorbent core (18) that wells upon absorbing bodily fluids, thereby maintaining pressure on the wound. All materials in all embodiments of the dressing are amenable to being sterilized. The wound-contacting layer (16) is positioned just as it is in the preferred embodiment.

Furthermore in lieu of a dressing (7), a fluid-filled sack capable of being heated or cooled and having a relatively high specific heat capacity could be contained within the holder (1).

We claim:

1. A bandage comprising:

a base portion, an aperture located on said base portion, means for releasably holding a dressing comprising a plurality of flaps, each of said flaps being attached at a proximal edge to said base portion and each of said flaps protruding from said base portion, said plurality of flaps having an open position in which said flaps are folded away from said aperture to permit access to said aperture from a distal side of the bandage, and said plurality of flaps having a closed position in which said flaps are folded toward said position in which said flaps are folded toward said aperture to cover said aperture, said plurality of flaps comprising at least one closable side flap and at least one closable end flap, at least one flap being releasably attachable to another flap when in said closed position such that said attached flaps form a protective closure over said aperture, said flaps being connected to each other only when in said closed position, and means for attaching the bandage to the body of a patient, said bandage further comprising a flat pad attached to a proximal side of said holder, said flat pad being oriented such that it protrudes beyond the sides of said holder when said flaps are in said closed position, said flat pad having adhesive on a proximal side for attaching to a patient's body, said flat pad being adapted to firmly anchor the bandage to a patient's body such that the bandage resists removal from a patient's body to which it is attached during manipulation of said flaps.

2. A bandage as recited in claim 1 wherein said flat pad comprises adhesive on a distal side, said adhesive being located and adapted for retaining said flaps against said flat pad said flaps are in said closed position.

3. A bandage as recited in claim 2 wherein said holding means is constructed from material that is transparent and gas-permeable, and wherein said aperture is oriented for unobstructed viewing from the distal side of the bandage when said flaps are in said open position.

4. A bandage comprising:

a holder constructed of material which is sufficiently flexible to accommodate attachment to various portions of a patient's body and to accommodate normal bodily movement of a patient without detaching from the patient's body, said holder comprising:

a generally rectangular-shaped base portion having four sides, an aperture located on said base portion, means for releasably holding a dressing comprising four flaps, each of said flaps being attached at a proximal edge to said base portion and each of said flaps protruding from said base portion, said plurality of flaps having an open position in which said flaps are folded away from said aperture to permit access to said aperture from the distal side of the bandage, and said plurality of flaps having a closed position in which said flaps are folded toward said aperture to cover said aperture, said plurality of flaps comprising at least one closable side flap and at least one closable end flap, at least one flap being releasably attachable to another flap when in said closed position such that said attached flaps form a protective closure over said aperture, said flaps being connected to each other only when in said closed position, and means for attaching the bandage to the body of a patient, said bandage further comprising a flat pad attached to a proximal side of said holder, said flat pad being oriented such that it protrudes beyond the sides of said holder when said flaps are in said closed position, said flat pad having adhesive on its proximal side for attaching to a patient's body, said flat pad being adapted to firmly anchor the bandage to a patient's body such that the bandage resists removal from a patient's body to which it is attached during manipulation of said flaps.

5. A bandage as recited in claim 4 wherein said aperture is oriented for unobstructed viewing from the distal side of the bandage when said flaps are in said open position.

6. A bandage as recited in claim 5;

wherein said holder and said flaps are constructed so that when said flaps are in said open position, said flaps lie in a position away from said aperture so that they do not contact a patient's wound observable through said aperture;

wherein said holder and said flaps are constructed so that said flat pad may be placed directly against a patient's wound from above the wound on the distal side of the bandage without the necessity of sliding the dressing across the wound; and wherein said flat pad comprises adhesive on a distal side, said adhesive being located and adapted for retaining said flaps against said flat pad when said flaps are in said closed position.

7. A bandage as recited in claim 6 wherein said flat pad has dimensions such that it covers more of the surface of the patient's skin than would be covered by the bandage without such flat pad.

8. A bandage as recited in claim 1 further comprising:
a fluid-filled sack capable of being heated or cooled and removably insertable into said means for holding a dressing.

* * * * *